(12) United States Patent
Miyoshi et al.

(10) Patent No.: US 10,406,183 B2
(45) Date of Patent: Sep. 10, 2019

(54) COMPOSITION COMPRISING CELL AND BIOCOMPATIBLE POLYMER

(71) Applicant: FUJIFILM Corporation, Minato-ku, Tokyo (JP)

(72) Inventors: Hayato Miyoshi, Ashigarakami-gun (JP); Ai Okamura, Ashigarakami-gun (JP); Ciara C. Tate, San Francisco, CA (US); Monique A. Dao, Mountain View, CA (US)

(73) Assignees: FUJIFILM Corporation, Tokyo (JP); SANBIO, INC., Mountain View, CA (US)

( * ) Notice: Subject to any disclaimer, the term of this patent is extended or adjusted under 35 U.S.C. 154(b) by 10 days.

(21) Appl. No.: 15/425,518

(22) Filed: Feb. 6, 2017

(65) Prior Publication Data

US 2017/0143767 A1    May 25, 2017

Related U.S. Application Data

(60) Continuation of application No. 14/739,483, filed on Jun. 15, 2015, now abandoned, which is a division of
(Continued)

(51) Int. Cl.
*A61K 35/30*     (2015.01)
*C12N 5/0797*     (2010.01)
(Continued)

(52) U.S. Cl.
CPC .............. *A61K 35/30* (2013.01); *A61K 38/39* (2013.01); *C12N 5/0622* (2013.01);
(Continued)

(58) Field of Classification Search
None
See application file for complete search history.

(56) References Cited

U.S. PATENT DOCUMENTS

| | | | |
|---|---|---|---|
| 6,989,271 B2 * | 1/2006 | Dezawa | A61L 27/383 424/93.7 |
| 7,052,875 B1 | 5/2006 | Terada et al. | |

(Continued)

FOREIGN PATENT DOCUMENTS

| | | |
|---|---|---|
| JP | 2003-144155 A | 5/2003 |
| JP | 2004-75547 A | 3/2004 |

(Continued)

OTHER PUBLICATIONS

Sakai, Shinji; et al; "An injectable, in situ enzymatically gellable, gelatin derivative for drug delivery and tissue engineering" Biomaterials, 30, 3371-3377, 2009 (Year: 2009).*
(Continued)

*Primary Examiner* — David W Berke-Schlessel
(74) *Attorney, Agent, or Firm* — Birch, Stewart, Kolasch & Birch, LLP

(57) ABSTRACT

It is an object of the present invention to provide a cell-containing composition capable of suppressing the outflow of the cells after transplantation and improving the survival rate of the cells. The present invention provides a composition which comprises any of bone marrow stromal cell-derived neural precursor cells, bone marrow stromal cell-derived Schwann cells, or bone marrow stromal cell-derived skeletal muscle cells; and a biocompatible polymer.

18 Claims, 5 Drawing Sheets

Specification includes a Sequence Listing.

Related U.S. Application Data application No. 13/085,128, filed on Apr. 12, 2011, now abandoned.

(51) Int. Cl.
*C12N 5/079* (2010.01)
*A61K 38/39* (2006.01)

(52) U.S. Cl.
CPC ........ *C12N 5/0623* (2013.01); *C12N 2501/01* (2013.01); *C12N 2501/115* (2013.01); *C12N 2501/13* (2013.01); *C12N 2501/135* (2013.01); *C12N 2501/385* (2013.01); *C12N 2501/42* (2013.01); *C12N 2506/1353* (2013.01); *C12N 2510/00* (2013.01); *C12N 2533/54* (2013.01)

(56) References Cited

U.S. PATENT DOCUMENTS 7,682,825 B2 * 3/2010 Dezawa ............... C12N 5/0619
435/373

2005/0079218 A1   4/2005 Gopferich et al.
2006/0216276 A1 * 9/2006 Dezawa ................. A61K 35/30
424/93.7
2012/0165263 A1   6/2012 Hiratsuka et al.

FOREIGN PATENT DOCUMENTS

| JP | 2005-513047 A | 5/2005 | |
| WO | WO 99/61063 A1 | 2/1999 | |
| WO | WO-2008103042 A1 * | 8/2008 | ............. C07K 14/78 |
| WO | WO 2008/133196 A1 | 11/2008 | |
| WO | WO 2009/116556 A1 | 9/2009 | |
| WO | WO 2011/027850 A1 | 3/2011 | |

OTHER PUBLICATIONS

Japanese Decision of Refusal for Japanese Application No. 2016-131476, dated Oct. 17, 2017, with a machine translation.
Japanese Office Action issued in Japanese Application No. 2016-131476 dated Apr. 18, 2017, together with an English translation thereof.

* cited by examiner

Figure 1: Scanning Electron Microscopic image of biocompatible polymer particles (dry state)
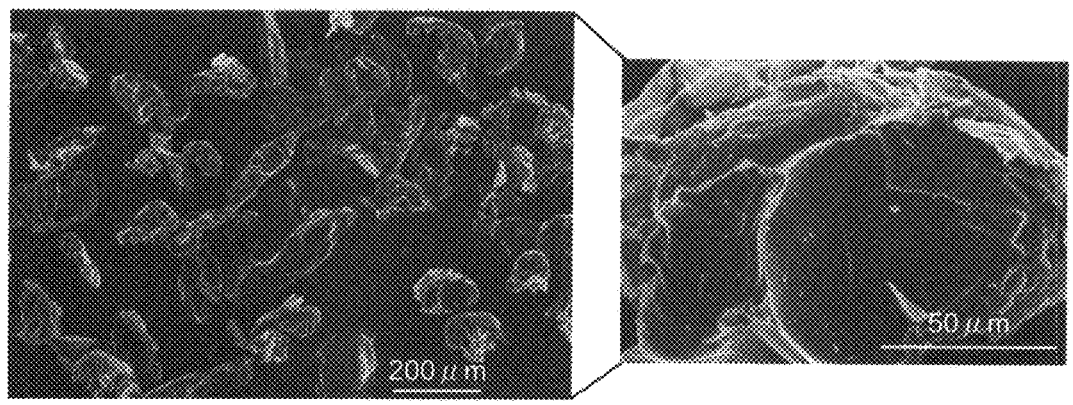
Figure 2: In Vitro Cell Viability on Rat Hippocampal Slice
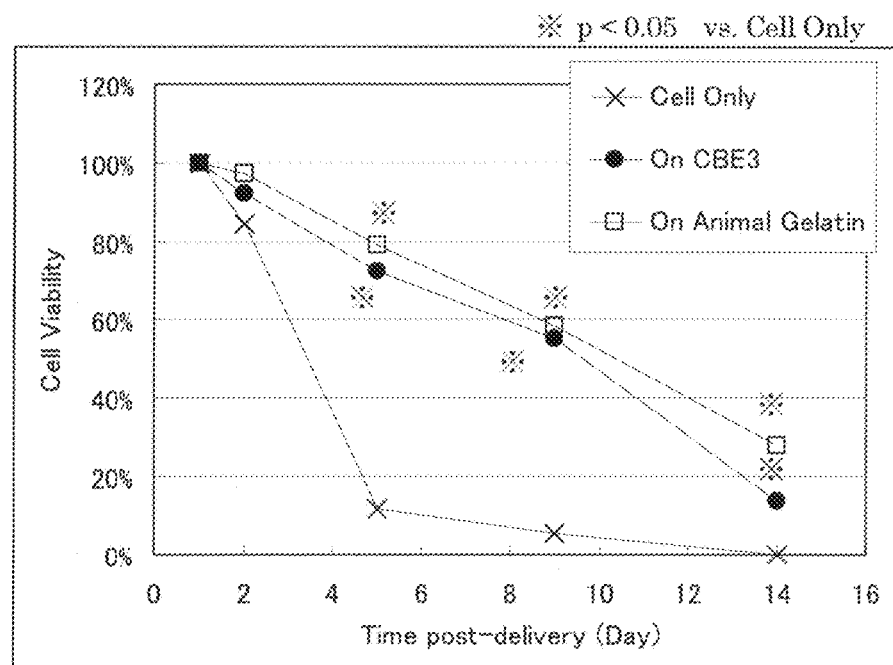

Figure 3: In Vitro Cell Viability in Ultra Low Attachment Culture Plate
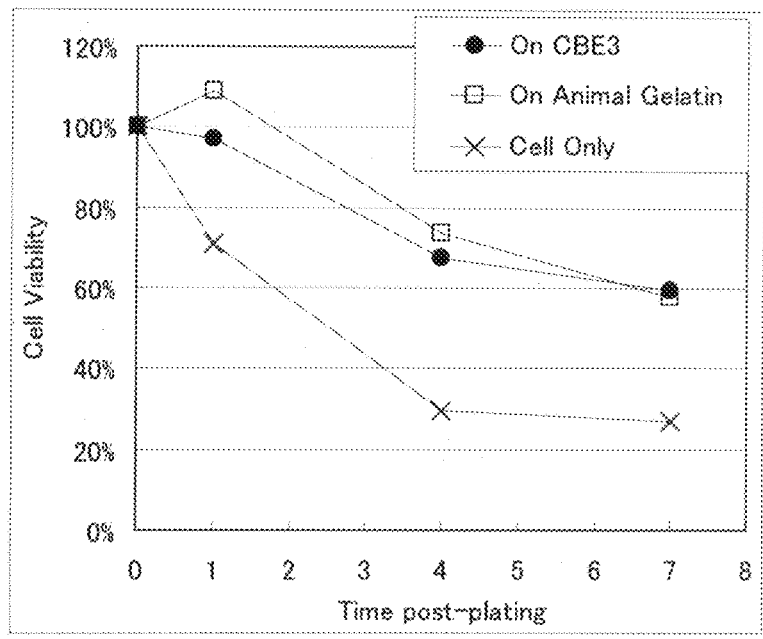
Figure 4: Cell Adhesion on biocompatible polymer particles
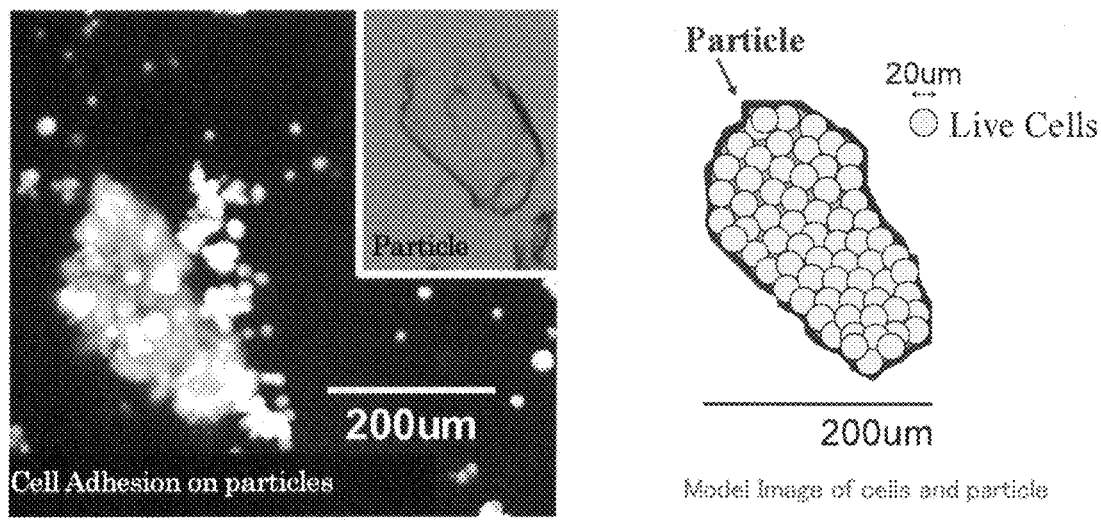
Cells are stained by Calsein-AM (Live Cells show fluorescence)
It was obvious that cells were attached on the particle.

Figure 5: Number of cells on biocompatible polymer particles
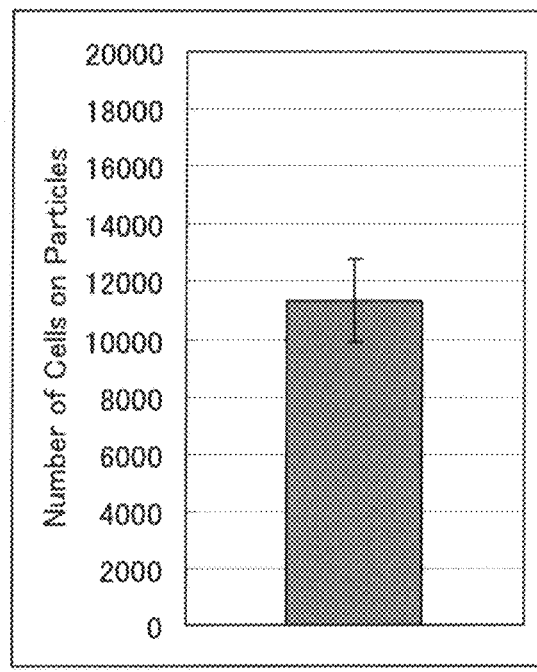
Figure 6: Transplanted Cell Viability in Rat Brain (1month post-TP)
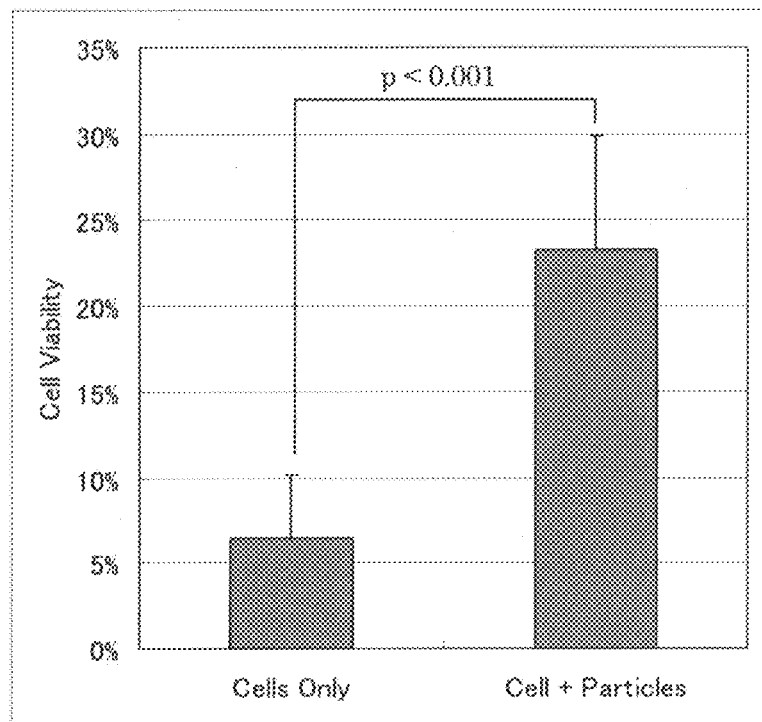

Figure 7: Regions for counting host neurons
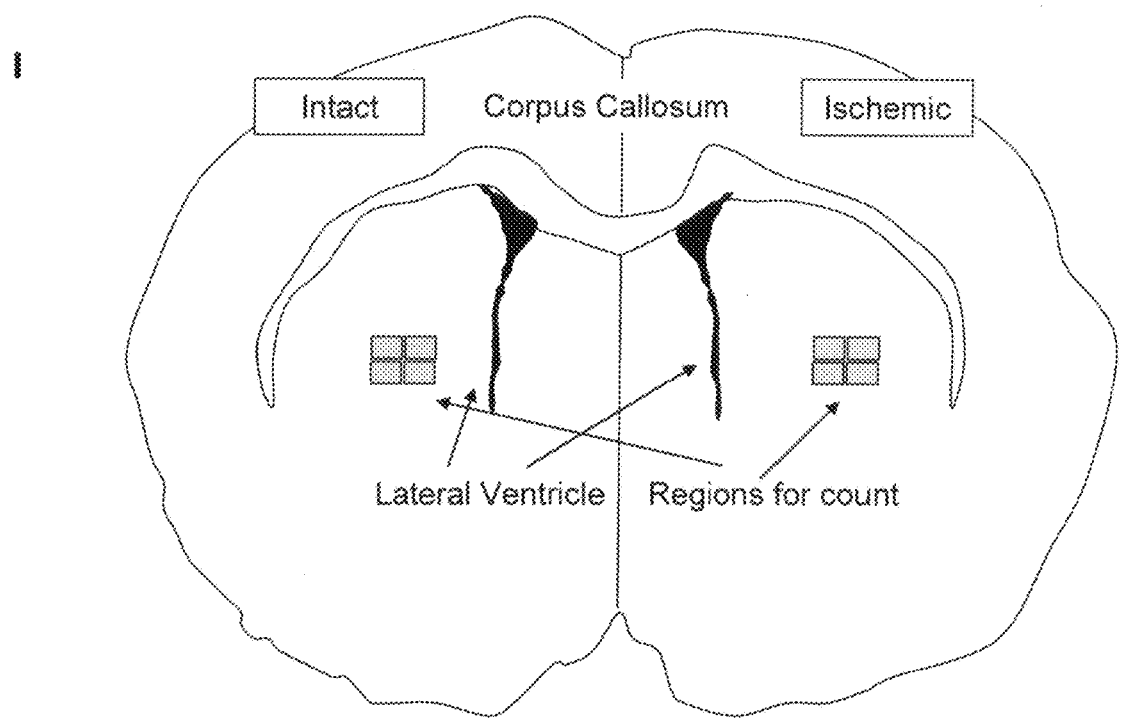
Figure 8: Preservation of host neurons (1 month post-TP)
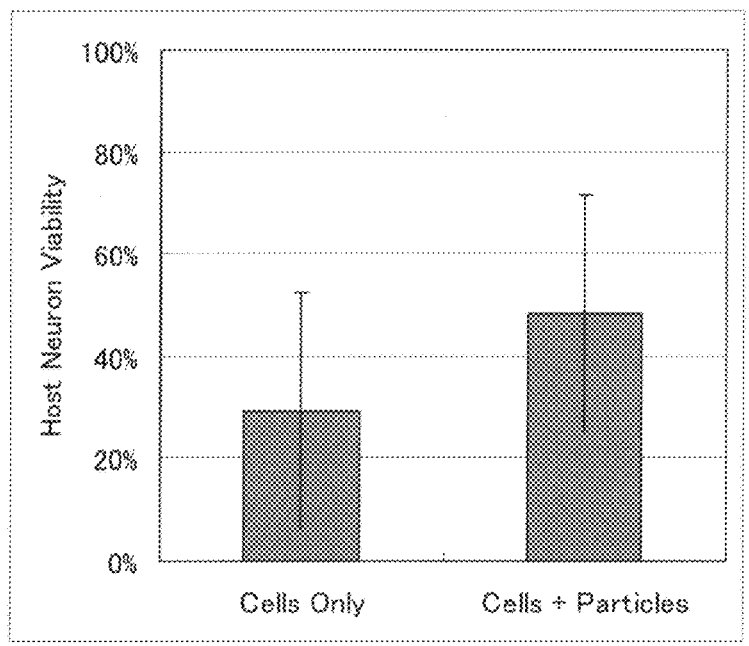
Host neuron Viability;
Percent of number of neurons in ischemic side standardized by number of neurons in intact side Figure 9: Preservation of mielin (1month post-TP)
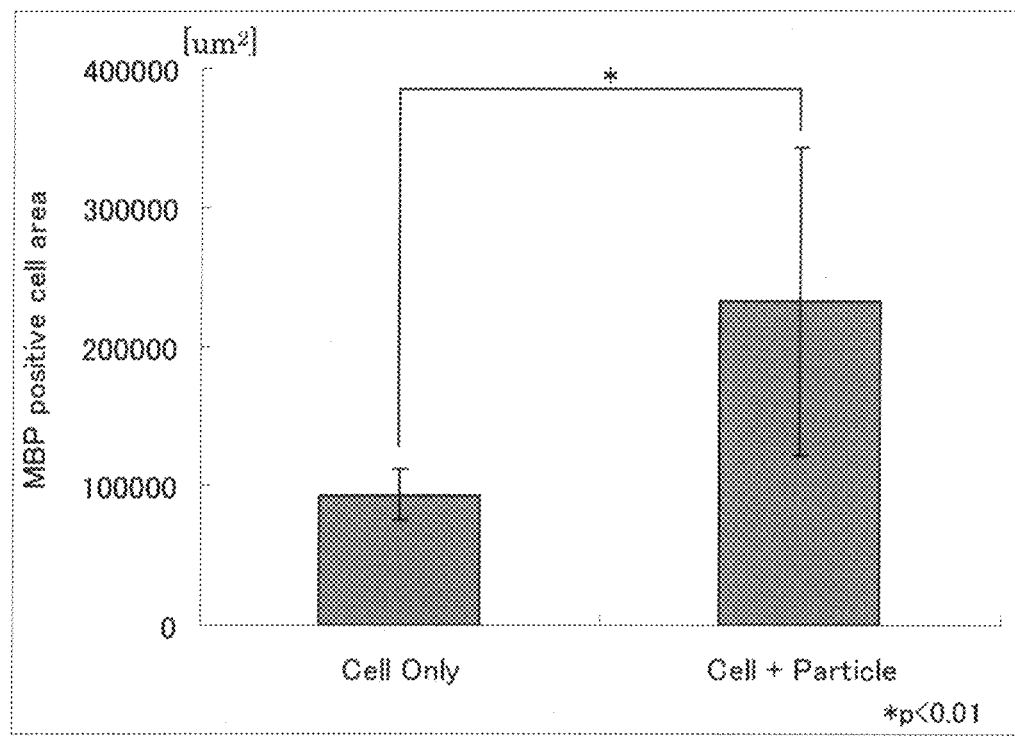
Figure 10: Cell Viability of SB618 on CBE3 or PDL coated glass
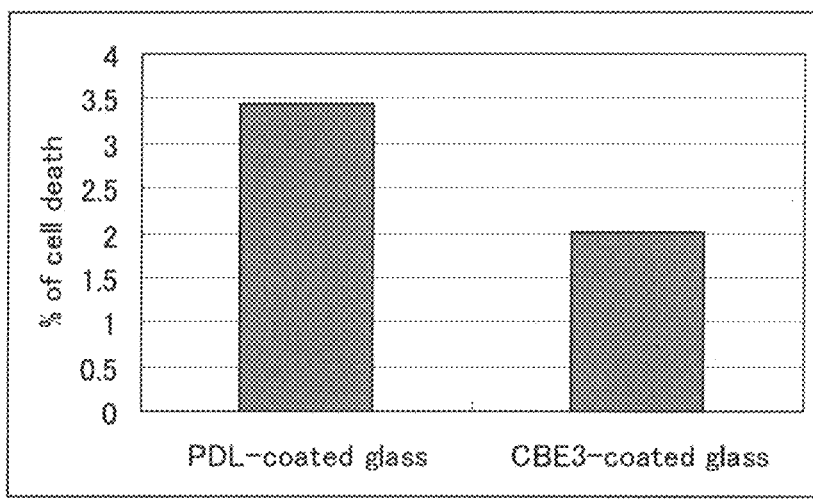

SEQUENCE LISTING

```
<160> NUMBER OF SEQ ID NOS: 1

<210> SEQ ID NO 1
<211> LENGTH: 571
<212> TYPE: PRT
<213> ORGANISM: Artificial
<220> FEATURE:
<223> OTHER INFORMATION: Recombinant CBE3 Gelatin

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
                20                  25                  30

Arg Gly Asp Ala Gly Pro Lys Gly Ala Asp Gly Ala Pro Gly Ala Pro
            35                  40                  45

Gly Leu Gln Gly Met Pro Gly Glu Arg Gly Ala Ala Gly Leu Pro Gly
        50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
                100                 105                 110

Asp Ala Gly Pro Lys Gly Ala Asp Gly Ala Pro Gly Lys Asp Gly Val
            115                 120                 125

Arg Gly Leu Ala Gly Pro Ile Gly Pro Pro Gly Pro Ala Gly Ala Pro
        130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
```

```
                    245                 250                 255
Glu Arg Gly Asp Ala Gly Pro Lys Gly Ala Asp Gly Ala Pro Gly Lys
                260                 265                 270

Asp Gly Val Arg Gly Leu Ala Gly Pro Ile Gly Pro Pro Gly Glu Arg
                275                 280                 285

Gly Ala Ala Gly Leu Pro Gly Pro Lys Gly Glu Arg Gly Asp Ala Gly
                290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Ala Gly Ala Pro Gly Ala Pro
                325                 330                 335

Gly Leu Gln Gly Met Pro Gly Glu Arg Gly Ala Ala Gly Leu Pro Gly
                340                 345                 350

Pro Lys Gly Glu Arg Gly Asp Ala Gly Pro Lys Gly Ala Asp Gly Ala
                355                 360                 365

Pro Gly Lys Asp Gly Val Arg Gly Leu Ala Gly Pro Pro Gly Ala Pro
                370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
                405                 410                 415

Lys Gly Ala Asp Gly Ala Pro Gly Ala Pro Gly Leu Gln Gly Met Pro
                420                 425                 430

Gly Glu Arg Gly Ala Ala Gly Leu Pro Gly Pro Lys Gly Glu Arg Gly
                435                 440                 445

Asp Ala Gly Pro Lys Gly Ala Asp Gly Ala Pro Gly Lys Asp Gly Val
        450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
                485                 490                 495

Ala Asp Gly Ala Pro Gly Lys Asp Gly Val Arg Gly Leu Ala Gly Pro
                500                 505                 510

Ile Gly Pro Pro Gly Pro Ala Gly Ala Pro Gly Ala Pro Gly Leu Gln
                515                 520                 525

Gly Met Pro Gly Glu Arg Gly Ala Ala Gly Leu Pro Gly Pro Lys Gly
                530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Pro Gly
                565                 570
```

COMPOSITION COMPRISING CELL AND BIOCOMPATIBLE POLYMER

CROSS REFERENCE TO RELATED APPLICATIONS

This application is a Continuation of copending Application Ser. No. 14/739,483, filed on Jun. 15, 2015, which is a Divisional of Application Ser. No. 13/085,128, filed Apr. 12, 2011, all of which are hereby expressly incorporated by reference into the present application.

TECHNICAL FIELD

The present invention relates to a composition which comprises any of bone marrow stromal cell-derived neural precursor cells, bone marrow stromal cell-derived Schwann cells, or bone marrow stromal cell-derived skeletal muscle cells; and a biocompatible polymer.

BACKGROUND ART

The injury of central nervous system tissues causes various types of diseases. For example, cerebral infarction is caused by the necrosis of brain tissues due to ischemia. Parkinson's disease is a neurodegenerative disease caused by degeneration of dopamine-producing cells existing in the substantia nigra in the midbrain. Spinal cord injury is mainly caused by damaging the spinal cord by strong external force.

The disorders of motor function, sensory function and cognitive function are generated as a result of the loss of central nervous system tissues. It is known that the central nervous system tissues have an extremely poor regenerative power. Thus, if these tissues are once injured, it is basically difficult to treat them. At present, rehabilitation and the like are undergone to recover lost function. However, it takes a long period of time to obtain the effects of such rehabilitation, and further, the recovery of disordered function is extremely difficult.

However, in recent years, the regeneration of the injured central nervous system tissues is attempted by transplantation of foreign cells (which are cells capable of differentiating into nervous cells, such as bone marrow stem cells, neural stem cells, ES cells, and adipose tissue-derived stein cells) (Nat Med 10: S42-S50, 2004).

U.S. Pat. No. 7,682,825 discloses a method of differentiating bone marrow stromal cells to neuronal precursor cells by introduction of notch gene. The inventors investigated stimulation of bone marrow stromal cells by introduction of genes which play a central role in the initial stages of morphogenesis of bone marrow stromal cells, and examined the effects of such stimulation on induction of bone marrow stromal cell differentiation. Specifically, it was expected to be potentially possible to "reset" bone marrow stromal cells by introduction of Notch genes and Notch signaling genes, which play important roles in developmental differentiation of the nervous system and perform functions in determining cell fates when precursor cells branch to neural cells or glial cells. It is important to note that despite implication of Notch genes and Notch signaling related genes in the mechanism of suppressing induction of cell differentiation, it was a completely unexpected finding that combining introduction of Notch genes and Notch signaling related genes with other stimulation to induce differentiation, can also induce differentiation of the very cells into which the Notch genes and Notch signaling related genes have been introduced (not the cells contacting with the cells into which the Notch genes and Notch signaling related genes have been introduced). It cannot be affirmed that introduction of the Notch genes and Notch signaling related genes in the differentiation inducing method of the present invention resulted in resetting of developmental differentiation of bone marrow stromal cells. However, by combination of this gene introduction with other differentiation inducing steps according to the invention, it was possible as a result to provide a method of efficiently inducing differentiation of bone marrow stromal cells to neural cells or skeletal muscle cells.

US2006/0216276 discloses a method of administering neuronal precursor cells transdifferentiated from marrow adherent stem cells by introduction of Notch intracellular domain gene to patients with injured central nervous system tissues, and particularly to patients with cerebral infarction. However, this method is problematic in that the cells flow out after transplantation, and also in that the survival rate of the transplanted cells is low. Among the transplanted cells, only a very small number of cells may survive as central nervous system tissues.

DISCLOSURE OF THE INVENTION

It is an object of the present invention to provide a cell-containing composition capable of suppressing the outflow of the cells after transplantation and improving the survival rate of the cells.

As a result of intensive studies directed towards achieving the aforementioned object, the present inventors have found that the object can be achieved by preparing a cell-containing composition, in which bone marrow stromal cells into which the Notch gene and/or Notch signaling related gene have been introduced that are used as cells to be transplanted are adhered to a biocompatible polymer, thereby completing the present invention.

The following invention is provided by the present invention.

[1] A composition which comprises: (A) any cells of the following (a), (b) and (c), and (B) a biocompatible polymer:

(a) bone marrow stromal cell-derived neural precursor cells which are obtained by (1) introducing a nucleic acid comprising Notch sequences, wherein said Notch sequences consist of sequences encoding a Notch intracellular domain, and (2) culturing said bone marrow stromal cells such that said bone marrow stromal cells differentiate into neural precursor cells, wherein the resultant differentiated cells are offspring of bone marrow stromal cells into which said nucleic acid has been introduced;

(b) bone marrow stromal cell-derived Schwann cells which are obtained by (1) collecting bone marrow stromal cells from bone marrow, and culturing said cells in a standard essential culture medium supplemented with a serum; (2) adding a reducing agent to said culture medium, and further culturing said cells; (3) adding retinoic acid to said culture medium, and further culturing said cells; and (4) adding forskolin, and/or a differentiation, survival and growth stimulating factor which acts on nerves and glial cells to said culture medium, and further culturing said cells to obtain said bone marrow stromal cell-derived Schwann cells; and (c) bone marrow stromal cell-derived skeletal muscle cells which are obtained by (1) adding (i) a cyclic AMP (cAMP) increasing agent or a cAMP analogue, and (ii) a cell differentiation stimulating factor comprising bFGF, PDGF-AA, and neuregulin to a culture of bone marrow stromal cells wherein said bone marrow stromal cells are not treated with a demethylating agent, and culturing the cells; (2) introducing a Notch gene into the cells obtained in (1), and culturing the cells to obtain a culture of myoblasts, provided that said culture does not contain a co-culture of the cells introduced with the gene and non-introduced cells; and (3) adding a Notch ligand to the culture of the myoblasts obtained in (2), and culturing the cells such that skeletal muscle cells are induced.

[2] The composition according to [1], wherein the biocompatible polymer is a gelatin.

[3] The composition according to [1], wherein the biocompatible polymer is a recombinant gelatin having an amino acid sequence derived from a partial amino acid sequence of collagen.

[4] The composition according to [3], wherein the recombinant gelatin has a repetition of a sequence characteristic for collagen represented by Gly-X—Y wherein each of X and Y independently represents any given amino acid, wherein a plurality of Gly-X—Y may be identical to or different from one another, and the recombinant gelatin has a molecular weight of 2 KDa to 100 KDa.

[5] The composition according to [3], wherein the recombinant gelatin has a repetition of a sequence characteristic for collagen represented by Gly-X—Y wherein each of X and Y independently represents any given amino acid, wherein a plurality of Gly-X—Y may be identical to or different from one another, and the recombinant gelatin has a molecular weight of 10 KDa to 90 KDa.

[6] The composition according to [3], wherein the recombinant gelatin has a repetition of a sequence characteristic for collagen represented by Gly-X—Y wherein each of X and Y independently represents any given amino acid, wherein a plurality of Gly-X—Y may be identical to or different from one another, and the recombinant gelatin comprises two or more sequences of cell adhesion signals in a single molecule.

[7] The composition according to [6], wherein the cell adhesion signal has an amino acid sequence represented by Arg-Gly-Asp.

[8] The composition according to [3], wherein the amino acid sequence of the recombinant gelatin does not comprise serine and threonine.

[9] The composition according to [3], wherein the amino acid sequence of the recombinant gelatin does not comprise serine, threonine, asparagine, tyrosine, and cysteine.

[10] The composition according to [3], wherein the amino acid sequence of the recombinant gelatin does not comprise an amino acid sequence represented by Asp-Arg-Gly-Asp.

[11] The composition according to [3], wherein the recombinant gelatin is represented by the following formula:

A-[(Gly-X—Y)$_n$]$_m$-B wherein A represents any given amino acid or amino acid sequence; B represents any given amino acid or amino acid sequence; each of an n number of X independently represents any given amino acid; each of an n number of Y independently represents any given amino acid; n represents an integer of 3 to 100; m represents an integer of 2 to 10; and further, an n number of Gly-X—Y may be identical to or different from one another.

[12] The composition according to [3], wherein the recombinant gelatin is represented by the following formula:

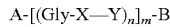

Gly-Ala-Pro-[(Gly-X—Y)$_{63}$]$_3$-Gly wherein each of 63 X units independently represents any given amino acid; each of 63 Y units independently represents any given amino acid; and 63 Gly-X—Y units may be identical to or different from one another.

[13] The composition according to [3], wherein the recombinant gelatin has: (1) the amino acid sequence shown in SEQ ID NO: 1, or (2) an amino acid sequence showing a homology of 80% or more with the amino acid sequence shown in SEQ ID NO: 1 and having the property of adhering to a nerve cell or a cell capable of differentiating a nerve cell.

[14] The composition according to [3], wherein the recombinant gelatin is crosslinked.

[15] The composition according to [3], wherein the crosslinking is carried out with an aldehyde, a condensing agent, or an enzyme.

[16] A method for treating nervous disease, which comprises administering to a patient suffering from nervous disease a therapeutically effective amount of a composition comprising (A) any cells of the following (a) and (b), and (B) a biocompatible polymer.

(a) bone marrow stromal cell-derived neural precursor cells which are obtained by (1) introducing a nucleic acid comprising Notch sequences, wherein said Notch sequences consist of sequences encoding a Notch intracellular domain, and (2) culturing said bone marrow stromal cells such that said bone marrow stromal cells differentiate into neural precursor cells, wherein the resultant differentiated cells are offspring of bone marrow stromal cells into which said nucleic acid has been introduced; and (b) bone marrow stromal cell-derived Schwann cells which are obtained by (1) collecting bone marrow stromal cells from bone marrow, and culturing said cells in a standard essential culture medium supplemented with a serum; (2) adding a reducing agent to said culture medium, and further culturing said cells; (3) adding retinoic acid to said culture medium, and further culturing said cells; and (4) adding forskolin, and/or a differentiation, survival and growth stimulating factor which acts on nerves and glial cells to said culture medium, and further culturing said cells to obtain said bone marrow stromal cell-derived Schwann cells; or

[17] The method according to [16], wherein the composition is administered locally.

[18] The method according to [16], wherein the composition is administered to the central nervous system of the patient.

[19] A method for treating muscular disease, which comprises administering to a patient suffering from muscular disease a therapeutically effective amount of a composition comprising (A) any cells of the following (c), and (B) a biocompatible polymer.

(c) bone marrow stromal cell-derived skeletal muscle cells which are obtained by (1) adding (i) a cyclic AMP (cAMP) increasing agent or a cAMP analogue, and (ii) a cell differentiation stimulating factor comprising bFGF, PDGF-AA, and neuregulin to a culture of bone marrow stromal cells wherein said bone marrow stromal cells are not treated with a demethylating agent, and culturing the cells; (2) introducing a Notch gene into the cells obtained in (1), and culturing the cells to obtain a culture of myoblasts, provided that said culture does not contain a co-culture of the cells introduced with the gene and non-introduced cells; and (3) adding a Notch ligand to the culture of the myoblasts obtained in (2), and culturing the cells such that skeletal muscle cells are induced.

[20] The method according to [19], wherein the composition is administered locally.

BRIEF DESCRIPTION OF THE DRAWINGS

FIG. 1 shows a SEM image of CBE3 particles (dry state).
FIG. 2 shows the promotion of cell viability on rat hippocampal slices.
FIG. 3 shows the promotion of cell viability on a ultra low attachment culture plate.
FIG. 4 shows the results obtained by staining CBE3 particles, to which the cells have adhered, with CellStain Calsein AM (manufactured by Invitrogen), and then observing the stained particles under a fluorescent microscope.
FIG. 5 shows the number of cells on CBE3 particles.
FIG. 6 shows the promotion of transplanted cell viability in rat brain by CBE3 particles.
FIG. 7 shows the regions for counting host neurons.
FIG. 8 shows the preservation of host neurons (1 month post-TP).
FIG. 9 shows the preservation of mielin (1 month post-TP).
FIG. 10 shows the cell viability of SB6 1 8 on CBE3 or PDL coated glass.

PREFERRED MODE FOR CARRYING OUT THE INVENTION

Hereinafter, the present invention will be more specifically described.
(I) Cells Used in the Present Invention
(a) Bone Marrow Stromal Cell-Derived Neural Precursor Cells;

Bone marrow stromal cell-derived neural precursor cells used in the present invention are obtained by (1) introducing a nucleic acid comprising Notch sequences, wherein said Notch sequences consist of sequences encoding a Notch intracellular domain, and (2) culturing said bone marrow stromal cells such that said bone marrow stromal cells differentiate into neural precursor cells, wherein the resultant differentiated cells are offspring of bone marrow stromal cells into which said nucleic acid has been introduced, as described in U.S. Pat. No. 7,682,825. The disclosure of U.S. Pat. No. 7,682,825 is incorporated herein by reference.

By introducing Notch genes and Notch singaling related genes into bone marrow stromal cells, by administration of various factors and cytokines believed to be involved in promoting neural differentiation, and by increasing intracellular CAMP which is considered to be a general trigger for initiation of differentiation, it was possible to successfully induce differentiation of bone marrow stromal cells to neural cells under in vitro culturing conditions. It is confirmed not only expression of MAP-2 and neurofilament which are specific to neural cells, but also expression of the neurotransmitter synthetase tyrosine hydroxylase and production of neurotransmitters such as acetylcholine, neuropeptide Y and substance P.

It is also possible to use such neuronal precursor cells obtained by (1) introducing a nucleic acid comprising Notch sequences, wherein said Notch sequences consist of sequences encoding a Notch intracellular domain, and (2) culturing said bone marrow stromal cells such that said bone marrow stromal cells differentiate into neural precursor cells, wherein the resultant differentiated cells are offspring of bone marrow stromal cells into which said nucleic acid has been introduced, for treatment of central nervous system lesions. It is possible to provide such neuronal precursor cells and administer those neuronal precursor cells to a patient suffering from a central nervous system lesion in an amount sufficient to facilitate functional recovery of the patient. It is described in US. Patent Application No. 2006/0216276, for example. The disclosure of US. Patent Application No. 2006/0216276 is incorporated herein by reference.

As described in U.S. Pat. No. 7,682,825, differentiation of bone marrow stromal cells can be induced to neural cells, dopaminergic neurons, acetylcholinergic neurons or skeletal muscle cells in vitro, by introducing a Notch gene and/or a Notch signaling related gene into the cells, wherein the resultant differentiated cells are the offspring of cell division of the bone marrow stromal cells into which the Notch gene and/or Notch signaling related gene have been introduced.

Further, bone marrow stomal cells can be induced to differentiate into neural precursor cells in vitro by the steps of:
(1) isolating bone marrow stromal cells from bone marrow, and culturing the cells in a standard essential culture medium supplemented with a serum; and
(2) introducing a Notch gene and/or a Notch signaling related gene into the cells, and further culturing the cells to produce neural precursor cells.

The isolated bone marrow stromal cells may be human cells.

The neural precursor cells produced by the aforementioned method can be used in the present invention.

In the present invention, the neural precursor cells which express the neural precursor cell markers GLAST, 3PGDH and nestin, may be used.

Further, bone marrow stromal cells can be induced to differentiate into neural cells in vitro by the steps of:
(1) isolating bone marrow stromal cells from bone marrow, and culturing the cells in a standard essential culture medium supplemented with a serum;
(2) introducing a Notch gene and/or a Notch signaling related gene into the cells, and further culturing the cells; and
(3) adding a cyclic AMP-augmenting agent or a cyclic AMP analogue, and/or a cell differentiation stimulating factor to the culture medium, and further culturing the cells to produce the neural cells, wherein the resultant differentiated cells are offspring of cell division of the bone marrow stromal cells into which the Notch gene and/or Notch signaling related gene have been introduced.

The standard essential culture medium may be an Eagle's alpha modified minimum essential medium, and the serum may be fetal bovine serum.

The introduction of the Notch gene and/or Notch signaling related gene may be accomplished by lipofection with a mammalian expression vector.

The aforementioned method may also comprise, between steps (2) and (3), a step of selecting cells into which the genes have been introduced, for a predetermined period of time.

The cyclic AMP-augmenting agent or cyclic AMP analogue may be forskolin, and its concentration may be 0.001 nM to 100 μM.

The cell differentiation stimulating factor may be selected from the group consisting of basic fibroblast growth factor (bFGF), ciliary neurotrophic factor (CNTF) and mixtures thereof. The concentration of the cell differentiation stimulating factor may be between 0.001 ng/mil and 100 μg/ml.

The isolated bone marrow stromal cells are preferably human cells.

The neural cells produced by the aforementioned method can be used in the present invention.

In the present invention, the neural cells which express the neural cell markers .beta.-tubulin isotype 3 and TuJ-1, may be used.

Further, bone marrow stromal cells can be induced to differentiate into dopaminergic neurons in vitro by the steps of:
(1) isolating bone marrow stromal cells from bone marrow, and culturing the cells in a standard essential culture medium supplemented with a serum;
(2) introducing a Notch gene and/or a Notch signaling related gene into the cells, and further culturing the cells;
(3) adding a cyclic AMP-augmenting agent or a cyclic AMP analogue, and/or a cell differentiation stimulating factor to the culture medium, and further culturing the cells to produce the neural cells;
(4) culturing the neural cells obtained in Step (3) in a standard essential culture medium supplemented with a serum; and
(5) adding glial derived neurotrophic factor (GDNF), and a cyclic AMP-augmenting agent or a cyclic AMP analogue, and/or a cell differentiation stimulating factor other than glial derived neurotrophic factor to the culture medium, and further culturing the cells to obtain dopaminergic neurons,
wherein the resultant dopaminergic neurons are offspring of bone marrow stromal cells into which the Notch gene and/or Notch signaling related gene have been introduced.

The standard essential culture medium in Step (4) may be an Eagle's alpha modified minimum essential medium. The serum in Step (4) may be fetal bovine serum.

The cyclic AMP-augmenting agent or cyclic AMP analogue in Step (5) may be forskolin. The concentration of the cyclic AMP-augmenting agent or cyclic AMP analogue in Step (5) may be between 0.001 nM and 100 µM.

The cell differentiation stimulating factor other than glial derived neurotrophic factor in Step (5) may be selected from the group consisting of basic fibroblast growth factor (bFG), platelet-derived growth factor-AA (PDGF-AA) and mixtures thereof.

The concentration of glial derived neurotrophic factor in (Step 5) may be between 0.001 ng/ml and 100 µg/ml, and is preferably between 1 ng/ml and 100 ng/ml. The concentration of the cell differentiation stimulating factor other than glial derived neurotrophic factor in Step (5) may be between 0.001 ng/ml and 100 µg/ml.

The isolated bone marrow stromal cells are preferably human cells.

The dopaminergic neurons produced by the aforementioned method may be used in the present invention.

Further, the bone marrow stromal cells can be induced to differentiate into acetylcholinergic neurons in vitro by the steps of:
(1) isolating bone marrow stromal cells from bone marrow, and culturing the cells in a standard essential culture medium supplemented with a serum;
(2) introducing a Notch gene and/or a Notch signaling related gene into the cells, and further culturing the cells;
(3) adding a cyclic AMP-augmenting agent or a cyclic AMP analogue, and/or a cell differentiation stimulating factor to the culture medium, and further culturing the cells to produce the neural cells;
(4) culturing the neural cells obtained in Step (3) in a standard essential culture medium supplemented with a serum; and
(5) adding nerve growth factor (NGF), and a cyclic AMP-augmenting agent or a cyclic AMP analogue, and/or a cell differentiation stimulating factor other than nerve growth factor to the culture medium, and further culturing the cells to obtain acetylcholinergic neurons, wherein the resultant acetylcholinergic neurons are offspring of bone marrow stromal cells into which the Notch gene and/or Notch signaling related gene have been introduced.

The standard essential culture medium in Step (4) may be an Eagle's alpha modified minimum essential medium. The serum in Step (4) may be fetal bovine serum.

The cyclic AMP-augmenting agent or cyclic AMP analogue in Step (5) may be forskolin. The concentration of the cyclic AMP-augmenting agent or cyclic AMP analogue in Step (5) may be between 0.001 nM and 100 µM.

The cell differentiation stimulating factor other than nerve growth factor in Step (5) may be selected from the group consisting of basic fibroblast growth factor (bFG), platelet-derived growth factor-AA (PDGF-AA) and mixtures thereof.

The concentration of nerve growth factor in (Step 5) may be between 0.001 ng/ml and 100 µg/ml, and is preferably between 1 ng/ml and 100 ng/ml. The concentration of the cell differentiation stimulating factor other than nerve growth factor in Step (5) may be between 0.001 ng/ml and 100 µg/ml.

The isolated bone marrow stromal cells are preferably human cells.

The acetylcholinergic neurons produced by the aforementioned method may be used in the present invention.

Further, the bone marrow stromal cells can be induced to differentiate into skeletal muscle cells in vitro by the steps of:
(1) isolating bone marrow stromal cells from bone marrow, and culturing the cells in a standard essential culture medium supplemented with a serum;
(2) adding a demethylating agent to the culture medium, and further culturing the cells; (3) adding a cyclic AMP-augmenting agent or a cyclic AMP analogue, and/or a cell differentiation stimulating factor to the culture medium, and further culturing the cells;
(4) introducing a Notch gene and/or a Notch signaling related gene into the cells, and further culturing the cells;
(5) co-culturing the cells into which the genes have been introduced, with non-treated bone marrow stromal cells into which the genes have not been introduced; and
(6) adding a cyclic AMP-augmenting agent or a cyclic AMP analogue to the culture medium, and further culturing the cells to obtain skeletal muscle cells, wherein the resultant differentiated cells are offspring of bone marrow stromal cells into which the Notch gene and/or Notch signaling related gene have been introduced.

The standard essential culture medium may be an Eagle's alpha modified minimum essential medium, and the serum may be fetal bovine serum.

The demethylating agent may be 5-azacytidine, and its concentration may be between 30 nmol/l and 300 µmol/l.

The cyclic AMP-augmenting agent or cyclic AMP analogue in Step (3) may be forskolin. The concentration of the cyclic AMP-augmenting agent or cyclic AMP analogue in Step (3) may be between 0.001 nM and 100 µM.

The cell differentiation stimulating factor may be selected from the group consisting of basic fibroblast growth factor (bFGF), platelet-derived growth factor-AA (PDGF-AA), heregulin, and mixtures thereof, and its concentration may be between 0.001 ng/ml and 100 µg/ml. The introduction of the Notch gene and/or Notch signaling related gene may be accomplished by lipofection with a mammalian expression vector.

The aforementioned method may also comprise, between steps (4) and (5), a step of selecting cells into which the genes have been introduced, for a predetermined period of time.

The cyclic AMP-augmenting agent or cyclic AMP analogue in Step (5) may be forskolin. The concentration of the cyclic AMP-augmenting agent or cyclic AMP analogue in Step (5) may be between 0.001 nM and 100 µM.

The isolated bone marrow stromal cells are preferably human cells.

The skeletal muscle cells produced by the aforementioned method may be used in the present invention.

(b) Bone Marrow Stromal Cell-Derived Schwann Cells

The bone marrow stromal cell-derived Schwann cells used in the present invention are obtained by (1) collecting bone marrow stromal cells from bone marrow, and culturing said cells in a standard essential culture medium supplemented with a serum; (2) adding a reducing agent to said culture medium, and further culturing said cells; (3) adding retinoic acid to said culture medium, and further culturing said cells; and (4) adding forskolin, and/or a differentiation, survival and growth stimulating factor which acts on nerves and glial cells to said culture medium, and further culturing said cells to obtain said bone marrow stromal cell-derived Schwann cells, as described in U.S. Pat. No. 6,989,271. The disclosure of U.S. Pat. No. 6,989,271 is incorporated herein by reference.

The density of the cells in step (1) may be 50% confluency, and the cells are preferably subcultured to four generations.

The standard essential culture medium may be Minimum Essential Medium Eagle Alpha Modification (M4526, Sigma) and the serum may be fetal calf serum (14-501F, Lot #61-1012, BioWhittaker Co.). The serum may be added to a concentration of 20%. The reducing agent is an SH reagent, and the SH reagent is preferably .beta.-mercaptoethanol (214-18, Lot#MOM7582, Nacalai Tesque). The concentration of the reducing agent may be 1 nM to 10 mM, preferably 10 nM to 5 mM and more preferably 100 µM to 2 mM. The culturing time in step (2) may be 1 hour to 5 days, preferably 12 to 48 hours and more preferably 18 to 30 hours. The aforementioned reagent concentration is the concentration in the culture medium with which the cells are in direct contact (same for reagents referred to hereunder).

The differentiation inducing agent may be retinoic acid (all-trans) (R-2625, Sigma). The differentiation inducing agent concentration may be 0.001 ng/ml to 1 µg/ml, preferably 1 ng/ml to 200 ng/ml and more preferably 10 ng/ml to 60 ng/ml. In step (3), the culture medium used in step (2) may be exchanged with fresh differentiation inducing agent-containing medium after step (2) has been completed. The fresh culture medium is identical to the culture medium used in step (1) except that it contains the differentiation inducing agent. The culturing time for step (3) may be 1 hour to 30 days, preferably 12 hours to 7 days and more preferably 2 to 4 days.

The cyclic AMP-augmenting agent or cyclic AMP analogue may be forskolin (344273, Calbiochem). The concentration of the cyclic AMP-augmenting agent or cyclic AMP analogue may be 0.001 µg/ml to 100 µg/ml, preferably 100 ng/ml to 50 µg/ml and more preferably 1 µg/ml to 10 µg/ml.

The glial cell differentiation and survival stimulating factor may be one selected from the group consisting of neuregulin, platelet-derived growth factor-AA (396-HB, Peprotech EC, Ltd.), basic fibroblast growth factor (100-18B, Peprotech EC, Ltd.) or mixtures thereof. Neuregulin is available as Heregulin™ (396-HB, R&D Corp.) The concentration of the glial cell differentiation and survival stimulating factor may be 0.001 ng/ml to 100 µg/ml, with a concentration of preferably 0.1 ng/ml to 100 ng/ml and more preferably 1 ng/ml to 10 µg/ml for platelet-derived growth factor-AA, and a concentration of preferably 10 ng/ml to 1 µg/ml and more preferably 100 ng/ml to 300 ng/ml for basic fibroblast growth factor. The culturing time in step (4) may be 1 hour to 30 days, and preferably 4 to 10 days.

The term "bone marrow stromal cells" refers to cells in the bone marrow which are not of the hemopoietic system and are considered capable of differentiating to cells of the bone, cartilage, etc. Bone marrow stromal cells are positive for Thy1.2 and (β1-integrin) and negative for CD34. They may be positive or negative for S-100 (calcium-binding protein). Antibodies for Thy1.2, β1-integrin and CD34 were used.

(c) Bone Marrow Stromal Cell-Derived Skeletal Muscle Cells

The bone marrow stromal cell-derived skeletal muscle cells used in the present invention are obtained by (1) adding (i) a cyclic AMP (cAMP) increasing agent or a cAMP analogue, and (ii) a cell differentiation stimulating factor comprising bFGF, PDGF-AA, and neuregulin to a culture of bone marrow stromal cells wherein said bone marrow stromal cells are not treated with a demethylating agent, and culturing the cells; (2) introducing a Notch gene into the cells obtained in (1), and culturing the cells to obtain a culture of myoblasts, provided that said culture does not contain a co-culture of the cells introduced with the gene and non-introduced cells; and (3) adding a Notch ligand to the culture of the myoblasts obtained in (2), and culturing the cells such that skeletal muscle cells are induced, as described in U.S. Pat. No. 7,718,429. The disclosure of U.S. Pat. No. 7,718,429 is incorporated herein by reference.

The bone marrow stromal cells used herein mean cells present in the bone marrow other than cells of the hemopoietic system, and they are considered to be potentially differentiable into osteocytes, chondrocytes, adipocytes and the like. Bone marrow stromal cells are identified by positivity (+) for Thy1 and 2, positivity (+) for β 1-integrin, and negativity (−) for CD34. A preparation method of bone marrow stromal cells is specifically explained in detail in Japanese Patent Unexamined Publication No. 2003-144155, those skilled in the art can easily obtain bone marrow stromal cells. For example, culture of bone marrow stromal cell can be prepared by extracting bone marrow stromal cell from the bone marrow, and culturing the cells in a standard basal medium supplemented with serum. For example, it is desirable to subculture bone marrow stromal cells for 3 to 4 generations, and then prepare a culture adjusted to a cell density of, for example, about 1700 cells/cm$^2$. As the standard basal medium, Eagle's alpha modified minimum essential medium and the like can be used, and as the serum, fetal bovine serum, or in the case of human, human serum can be used. The bone marrow stromal cells need not be treated with the demethylating agent.

As the cAMP increasing agent or the cAMP analogue, for example, forskolin can be used, but not limited thereto. One or more kinds of cAMP increasing agents or cAMP analogues can be appropriately used. Although a concentration of the cAMP increasing agent or the cAMP analogue is not particularly limited, the concentration may be, for example, about 0.001 nM to 100 µM, preferably about 500 nM to 50 µM. As the cell differentiation stimulating factor, for example, basic fibroblast growth factor (bFGF), platelet-derived growth factor-AA (PDGF-AA), neuregulin (trade name: Heregulin), and the like can be used, and two or more kinds of these substances may be used in combination. Although a concentration of the cell differentiation stimulating factor is not particularly limited, the concentration may be, for example, about 0.001 ng/ml to 100 µg/ml, preferably about 0.5 ng/ml to 2 µg/ml. It is also preferable to use the cell differentiation stimulating factor in combination with the cAMP increasing agent or the cAMP analogue. For example, forskolin (5 µM), bFGF (10 ng/ml), PDGF-AA (5 ng/ml) and neuregulin (200 ng/ml) are added to the MEM Eagle Modification medium containing 10% fetal bovine serum (FBS), and bone marrow stromal cells are cultured therein. Pax7 as a marker of skeletal muscle stem cells comes to be expressed in this stage, and by using the marker as an index, the addition of the aforementioned agents and the culture can be performed.

Introduction of the Notch gene and/or Notch signaling related gene may be attained by, for example, lipofection using an expression vector for mammalian cells. However, the method is not limited to the above method, and a suitable gene introduction means can be employed. For example, the pCI-neo-NICD plasmid containing the Notch cytoplasm domain (MCD) cDNA (plasmid described in Japanese Patent Unexamined Publication No. 2003-144155, Example 1) can be introduced. After the aforementioned gene introduction, cells introduced with the gene can be preferably selected. This selection can be performed, for example, on the basis of neomycin resistance by adding G418 sulfate, and usually completed in about 10 to 14 days. The selected cells are desirably cultured until they reach 100% confluence. The cells obtained as described above constitute a myoblast population, and the cells are transformed so that transcription factors as skeletal muscle markers such as MyoD and myogenin come to be detectable. After the gene introduction or the aforementioned selection, the method described in Japanese Patent Unexamined Publication No. 2003-144155 employs the step of coculture of the cells after introduction with the gene and cells not introduced with the gene. Whilst, the aforementioned co-culture is not carried out in the method of the present invention.

Then, fusion induction for inducing mature skeletal muscle cells from the resulting myoblasts is performed according to the step (3). This step can be performed by adding a Notch ligand to the culture of myoblasts and culturing the cells. As the Notch ligand, for example, Jagged 1 protein (Lindsell, C. E. et al., Cell, 80, pp. 909-917, 1995) can be used. Although a concentration of Jagged 1 protein is not particularly limited, the concentration may be, for example, about 1 to 20 µg/ml, preferably about 5 µg/ml. A type of the medium is not particularly limited, and an ordinary basal medium, for example, MEM Eagle modification medium and the like can be used. Although about 10% of serum such as FBS can be added to the medium, a serum free medium can be preferably used. By using, for example, a serum free medium such as TTS-serum free medium (Yoshida, N. et al., J. Cell Sci., 111, pp. 769-779, 1998), skeletal muscle cells suitable for clinical application can be prepared. As a result of the aforementioned fusion induction, polynuclear skeletal muscle cells expressing mature markers such as Myf6/MRF4 and positive to the myosin heavy chain and skeletal myosin are induced. These skeletal muscle cells show spontaneous constriction movements during the culture. In the method described in Japanese Patent Unexamined Publication No. 2003-144155, cells after introduction with the gene and the cells not introduced with the gene are co-cultured, and then the cAMP increasing agent or the cAMP analogue is added to the culture to induce differentiation into mature skeletal muscle cells. However, in the method of the present invention, it is not necessary to add the cAMP increasing agent or the cAMP analogue to the culture.

Then, the skeletal muscle cells can be cloned by performing limiting dilution of the resulting culture of the skeletal muscle cells to a density of 1 cell per well, and a population of polynuclear skeletal muscle cells having the constriction ability can be obtained again from the living clones, which are usually obtained at a ratio of about 90%. The resulting cell population is a population substantially purely consisting of muscle cells, and not containing any other elements, and can be preferably used, in particular, for a purpose of therapeutic treatment of a muscular disease and the like. Furthermore, the resulting cell population contains skeletal muscle stem cells, and muscle cells can be stably prepared therefrom even after multiple times of subculture.

(II) Biocompatible Polymer

The biocompatible polymer used in the present invention may be either a protein, a polyamino acid, a glucide, or a biocompatible synthetic polymer.

The type of the protein is not particularly limited. A protein having a lysine residue and a glutamine residue is preferable. A protein having a molecular weight from approximately 10,000 to 1,000,000 is preferably used. Specific examples of such protein will be given below. However, proteins used in the present invention are not limited thereto. At least one type of protein selected from the group consisting of collagen, gelatin, acid-treated gelatin, albumin, ovalbumin, casein, casein sodium, transferrin, globulin, fibroin, fibrin, laminin, fibronectin and vitronectin may be used. The origin of such protein is not particularly limited. Any protein of a human, a bovine, a swine or fish, or a recombinant protein may be used. When casein is used in the present invention, the origin of the casein is not particularly limited. It may be derived from either milk or beans. As such casein, α-casein, β-casein, γ-casein, κ-casein and a mixture thereof may be used. Such casein may be used singly or in combination of two or more types. The protein used in the present invention may be used singly or in combination of two or more types.

Examples of the polyamino acid include polyaspartic acid, polyglutamic acid, and polylysine.

Examples of the glucide include polygalacturonic acid, heparin, chondroitin sulfate, hyaluronic acid, dermatan sulfate, chondroitin, dextran sulfate, cellulose sulfate, alginic acid, dextran, carboxymethyl chtin, galactomannan, gum arabic, Tragacanth gum, gellan gum, gellan sulfate, karaya gum, carrageenan, agar, xanthane gum, curdlan, pullulan, cellulose, starch, carboxymethyl cellulose, methyl cellulose, glucomannan, chitin, chitosan, xyloglucan and lentinan.

Examples of the synthetic polymer include aliphatic esters [for example, polyglycolic acid, polylactic acid, polycaprolactone, polydioxanone, trimethylene carbonate, poly(butylene succinate), poly(ethylene succinate), and copolymer thereof], aliphatic polycarbonates [for example, poly(butylene carbonate), and poly(ethylene carbonate)], and vinyl polymerized polymers [for example, polyethylene, polypropylene, polystyrene, polyacrylate, polymethacrylate, polyacrylamide, polymethacrylamide, polyvinyl chloride, polyvinylidene chloride, polyvinyl ether, polyvinyl carbazole, polyvinyl acetate and polyvinyl alcohol].

In the present invention, gelatin having an amino acid sequence which is derived from partial amino acid sequence of collagen can be used. Any naturally-occurring collagen can be used. Preferably, collagen type I, type II, type III, type IV and type V can be used. More preferably, collagen type I, type II and type III can be used. According to another aspect, the origin of the collagen is preferably human, bovine, pig, mouse, or rat. More preferably, the origin is human.

The type of gelatin used in the present invention is not particularly limited, so long as it comprises an amino acid sequence which is derived from partial amino acid sequence of collagen. Preferably, the gelatin comprises GXY region which is a feature of collagen. The GXY region which is a feature of collagen is a highly specific partial structure as compared with different proteins, in the amino acid composition and sequence of gelatin/collagen. Glycine accounts for about one third part of the total in the GXY region. Glycine is repeated every third in the amino acid sequence. Glycine is the simplest amino acid. Limitation as to the position in a molecular chain is small, and glycine greatly contributes to regeneration of helix structure during gelation. The amino acids represented by X and Y comprises many imino acids (praline, oxyproline). The imino acids account for 10% to 45% of the total.

The gelatin used in the present invention may be a gelatin which is derived from natural animal or may be a recombinant gelatin. When a gelatin which is derived from natural animal is used, the origin of the gelatin is not particularly limited. The origin may be any animal such as fish, bovine, pig or goat.

Among the above, a recombinant gelatin is particularly preferably used as a biocompatible polymer. Since the recombinant gelatin is not derived from an animal but is an artificial gelatin, it is highly biocompatible material where exogenous infection is avoided.

As the recombinant gelatin used in the present invention, a recombinant gelatin having an amino acid sequence derived from a partial amino acid sequence of collagen may be used. For example, those described in EP1014176A2, U.S. Pat. No. 6,992,172, WO2004-85473, WO2008/103041, etc. may be used. However, examples are not limited thereto. A preferred recombinant gelatin used in the present invention has the following feature.

Because of the original properties of a natural gelatin, the recombinant gelatin used in the present invention has excellent biocompatibility. Moreover, since the recombinant gelatin used in the present invention is not directly derived from natural products, it does not have risk factors such as BSE, and it has excellent non-infectivity. Furthermore, the recombinant gelatin used in the present invention is more uniform than a natural gelatin. Since the sequence of the recombinant gelatin used in the present invention has been determined, the present recombinant gelatin can be designed by the below-mentioned crosslinking or the like, precisely, with a less deviation in terms of strength and degradability.

The molecular weight of the recombinant gelatin used in the present invention is preferably from 2 KDa or more to 100 KDa or less. It is more preferably from 2.5 KDa or more to 95 KDa or less, further preferably from 5 KDa or more to 90 KDa or less, and most preferably from 10 KDa or more to 90 KDa or less.

The recombinant gelatin used in the present invention preferably has a repetition of a sequence characteristic for collagen represented by Gly-X—Y. Herein, a plurality of Gly-X—Y may be identical to or different from one another. In Gly-X—Y, Gly represents glycine, and each of X and Y represents any given amino acid (preferably, any given amino acid other than glycine). The Gly-X—Y sequence characteristic for collagen means a partial structure, which is extremely unique in comparison with other proteins, with regard to the amino acid compositions and sequences of gelatin and collagen. In this portion, glycine accounts for approximately one third of all amino acids, and thus glycine repeatedly appears every three amino acids in the amino acid sequence. Glycine is the simplest amino acid, and it is rather free from the constraints of molecular chain conformation. Thus, glycine greatly contributes to the regeneration of a helix structure in gelation. The amino acids represented by X and Y comprise large quantities of imino acids (proline and oxyproline), and such imino acids preferably account for 10% to 45% of all amino acids. It is preferable that a repeated structure of GXY account for preferably 80% or more, more preferably 95% or more, and most preferably 99% or more of the amino acids of the sequence.

A common gelatin comprises charged polar amino acids and uncharged polar amino acids at a ratio of 1:1. Herein, such polar amino acids specifically include cysteine, aspartic acid, glutamic acid, histidine, lysine, asparagine, glutamine, serine, threonine, tyrosine, and arginine. Of these, polar uncharged amino acids are cysteine, asparagine, glutamine, serine, threonine, and tyrosine. Polar amino acids account for preferably 10% to 40% of, and more preferably 20% to 30% of all amino acids that constitute the recombinant gelatin used in the present invention. On the other hand, the percentage of uncharged polar amino acids is preferably from 5% or more to less than 20%, and more preferably less than 10% in such polar amino acids. Moreover, it is preferable that any one amino acid, and preferably, two or more amino acids selected from serine, threonine, asparagine, tyrosine, and cysteine be not contained in the sequence.

In general, a minimum amino acid sequence acting as a cell adhesion signal in a polypeptide has been known (for example, "Byotai Seiri (Pathological Physiology)," Vol. 9, No. 7 (1990), p. 527, Nagai Shuppan). The recombinant gelatin used in the present invention preferably has two or more of such cell adhesion signals in a single molecule thereof. As such minimum amino acid sequence, a sequence, to which many types of cells can adhere, is preferable. Specifically, an RGD sequence, an LDV sequence, an REDV sequence, a YIGSR sequence, a PDSGR sequence, an RYVVLPR sequence, an LGTIPG sequence, an RNIAEIIKDI sequence, an IKVAV sequence, an LRE sequence, a DGEA sequence, and an HAV sequence are preferable. More preferably, an RGD sequence, a YIGSR sequence, a PDSGR sequence, an LGTIPG sequence, an IKVAV sequence, and an HAV sequence are used. Particularly preferably, an RGD sequence is used. With regard to such RGD sequence, an ERGD sequence is preferable. These sequences are indicated with single characters each representing amino acids.

With regard to the positions of the RGD sequences in the recombinant gelatin used in the present invention, the number of amino acids between the RGD sequences is between 0 and 100, and preferably between 25 and 60. The number of such amino acids is preferably ununiform.

From the viewpoint of cell adhesion and proliferative ability, with regard to the content of the minimum amino acid sequence, a single molecule of protein comprises preferably 3 to 50, more preferably 4 to 30, particularly preferably 5 to 20, and most preferably 12 amino acids.

In the recombinant gelatin used in the present invention, the percentage of GRD motif in the total number of amino acids is preferably at least 0.4%. When the recombinant gelatin contains 350 or more amino acid residues, each stretch of 350 amino acids preferably contains at least one RGD motif. The percentage of the RGD motif in the total number of amino acids is more preferably at least 0.6%, further preferably at least 0.8%, further preferably at least 1.0%, further preferably at least 1.2%, and further most preferably at least 1.5%. The number of the RGD motif per 250 amino acids in the recombinant gelatin is preferably at least 4, further preferably at least 6, further preferably at least 8, further preferably 12 to 16. The percentage of RGD motif which is 0.4% corresponds to at least one ROD sequence per 250 amino acids. The number of the RGD motif must be an integer, and therefore the gelatin which consists of 251 amino acids must at least 2 ROD sequences in order that the feature of 0.4% is fulfilled. Preferably, the recombinant gelatin of the present invention contains at least 2 RGD sequences per 250 amino acids, and more preferably at least 3 RGD sequences per 250 amino acids, and further preferably at least 4 ROD sequences per 250 amino acids. According to another embodiments, the recombinant gelatin of the present invention contains at least 4 RGD motifs, preferably at least 6 RGD motifs, more preferably at least 8 RGD motifs, and further preferably 12 to 16 RGD motifs.

Furthermore, the recombinant gelatin may be partially hydrolyzed.

The recombinant gelatin used in the present invention preferably has a repeated structure of A[(Gly-X—Y)$_n$]$_m$B. The letter m represents preferably 2 to 10, and more preferably 3 to 5. The letter n represents preferably 3 to 100, more preferably 15 to 70, and most preferably 50 to 65.

A plurality of naturally-existing collagen sequence units preferably bind to a repeating unit.

As a naturally-existing collagen used herein, any type of collagen may be used, as long as it exists in the nature. It is preferably type I, type II, type III, type IV, and type V. It is more preferably type I, type II, and type III. In another embodiment, the origin of such collagen is preferably a human, a bovine, a swine, a mouse, and a rat. It is more preferably a human.

The isoelectric point of the recombinant gelatin used in the present invention is preferably 5 to 10, more preferably 6 to 10, and further preferably 7 to 9.5.

Preferably, the recombinant gelatin has not been deamidated.

Preferably, the recombinant gelatin does not have procollagen.

Preferably, the recombinant gelatin does not have a telopeptide.

Preferably, the recombinant gelatin is a substantially pure collagen material prepared with a nucleic acid encoding a natural collagen.

The recombinant gelatin used in the present invention is particularly preferably a recombinant gelatin, which has:
(1) the amino acid sequence shown in SEQ ID NO: 1; or
(2) an amino acid sequence showing a homology of 80% or more (more preferably 90% or more, and most preferably 95% or more) with the amino acid sequence shown in SEQ ID NO: 1 and having the ability to adhere to a nerve cell or a cell capable of differentiating into a nerve cell.

The recombinant gelatin used in the present invention can be produced by a gene recombination technology known to persons skilled in the art. For example, it can be produced according to the methods described in EP1014176A2, U.S. Pat. No. 6,992,172, WO2004-85473, WO2008/103041, and the like. Specifically, a gene encoding the amino acid sequence of a certain recombinant gelatin is obtained, and the gene is then incorporated into an expression vector to produce a recombinant expression vector. Thereafter, the recombinant expression vector is introduced into a suitable host to produce a transformant. The obtained transformant is cultured in an appropriate medium, so that a recombinant gelatin can be generated. Thus, by recovering such recombinant gelatin generated from the culture, the recombinant gelatin used in the present invention can be produced.

Depending on intended use, the recombinant gelatin used in the present invention can be chemically modified. Examples of chemical modification include: the introduction of low molecular weight compounds or various types of polymers (biopolymers (a sugar and a protein), synthetic polymers, and polyamide) into a carboxyl group or an amino group on the side chain of the recombinant gelatin; and crosslinking between such recombinant gelatins. For the introduction of a low molecular weight compound into the recombinant gelatin, a carbodiimide condensing agent may be used, for example.

The type of a crosslinker used in the present invention is not particularly limited, as long as the present invention can be carried out with the use of the crosslinker. It may be either a chemical crosslinker or an enzyme. Examples of a chemical crosslinker include formaldehyde, glutaraldehyde, carbodiimide, and cyanamide. Of these, formaldehyde and glutaraldehyde are preferable. Moreover, such crosslinking between the recombinant gelatins includes: light irradiation to gelatin into which a photoreactive group has been introduced; and light irradiation in the presence of a photosensitizer. Examples of a photoreactive group include a cinnamyl group, a coumarin group, a dithiocarbamyl group, a xanthene dye, and camphorquinone.

When crosslinking is carried out using an enzyme, the type of the used enzyme is not particularly limited, as long as it has an action to crosslink between recombinant gelatin chains. Cross linking can be carried out preferably using transglutaminase and laccase, and most preferably using transglutaminase. Specific examples of a protein enzymatically crosslinked with transglutaminase are not particularly limited, as long as such protein has a lysine residue and a glutamine residue. Transglutaminase may be derived from either a mammal or a microorganism. Specific examples of such transgluminase include: a series of Active products manufactured by Ajinomoto Co., Inc.; mammal-derived transglutaminases that are available as reagents, such as guinea pig liver-derived transglutaminase, goat-derived transglutaminase, rabbit-derived transglutaminase, etc., which are manufactured by Oriental Yeast Co., Ltd., Upstate USA Inc., Biodesign International, etc.; and human-derived blood coagulation factors (Factor XIIIa; Haematologic Technologies, Inc.).

Crosslinking between the recombinant gelatins has two steps, namely, a step of mixing a solution of the recombinant gelatin with a crosslinker and a step of performing the reaction of the homogeneous mixed solution.

In the present invention, a mixing temperature at which the recombinant gelatin is treated with a crosslinker is not particularly limited, as long as the solution can be uniformly stirred at the temperature. Such mixing temperature is preferably 0° C. to 40° C., more preferably 0° C. to 30° C., further preferably 3° C. to 25° C., still further preferably 3° C. to 15° C., still further preferably 3° C. to 10° C., and particularly preferably 3° C. to 7° C.

After the recombinant gelatin and the crosslinker have been stirred, the temperature can be increased. A reaction temperature is not particularly limited, as long as crosslinking progresses at the temperature. Taking into consideration the degeneration or decomposition of the recombinant gelatin, the reaction temperature is substantially 0° C. to 60° C., more preferably 0° C. to 40° C., further preferably 3° C. to 25° C., still further preferably 3° C. to 15° C., still further preferably 3° C. to 10° C., and particularly preferably 3° C. to 7° C.

In the present invention, the aforementioned biocompatible polymer (preferably, a recombinant gelatin having an amino acid sequence derived from a partial amino acid sequence of collagen) can be administered in the form of a composition, in which the biocompatible polymer is combined with a nerve cell or a cell capable of differentiating into a nerve cell, to a target (for example, a human, and preferably, a patient with nervous disease) who requires the transplantation of the aforementioned nerve cell or cell capable of differentiating into such nerve cell.

(3) Use of the Composition of the Present Invention

The composition of the present invention comprises a composition which comprises any of the bone marrow stromal cell-derived neural precursor cells, the bone marrow stromal cell-derived Schwann cells or the bone marrow stromal cell-derived skeletal muscle cells, and a biocompatible polymer. In addition to them, the present composition may comprise a pharmaceutically acceptable carrier, as necessary. Examples of such pharmaceutically acceptable carrier include: a sterilized isotonic buffer, FRS, Isolite, a sterilized diluted solution such as water or a normal saline, fixed oil, polyethylene glycol, glycerin, propylene glycol, and other synthetic solvents; antibacterial or antifungal agents such as ascorbic acid, thimerosal, trimethoprim-sulfamethoxazole, nalidixic acid, methenamine hippurate, or nitrofurantoin macrocrystal; antioxidants such as ascorbic acid or sodium bisultite; chelating agents such as EDTA; buffers such as acetate, citrate, or phosphate; and active substances for adjusting tonicity, such as sodium chloride or dextrose. However, examples of the pharmaceutically acceptable carrier are not limited thereto. The pH of the composition of the present invention can be adjusted with acids or bases, such as hydrochloric acid or sodium hydroxide.

The formulation type of the composition of the present invention is preferably particle. When the composition of the present invention is administered via intravenous administration, suitable pharmaceutically acceptable carriers include a normal saline, normasol, Isolite, Plasmalite, and a phosphate buffered saline (PBS). When the composition of the present invention is administered via intravenous administration, the composition of the present invention has preferably been sterilized, and it needs to be fluidal to such an extent that it can be easily administered via injection.

The number of cells in the composition of the present invention can be determined to be the number of cells which is calculated so as to obtain desired therapeutic effects. The number of cells in the composition of the present invention per administration is preferably approximately 1,000 to approximately a billion cells, more preferably approximately 10,000 cells to approximately 100,000,000 cells, and further preferably approximately 50,000 cells to approximately 50,000,000 cells. The concentration of cells in the composition of the present invention is preferably approximately 100 cells/μL to approximately 100,000 cells/μL, and more preferably approximately 1,000 cells/4, to approximately 50,000 cells/μL.

The administration route of the composition of the present invention is not particularly limited. Local administration (for example, transplantation of the present composition into a site to be treated, etc.) or systemic administration (for example, intravenous injection, etc.) may be applied. Local administration (for example, transplantation of the present composition into a site to be treated, etc.) may be preferred.

Transplantation of the present composition can be carried out by various methods, such as injection using an injection cannula, a needle, or a shunt. However, examples are not limited thereto. When the composition of the present invention is administered via systemic administration, parenteral administration, such as intravenous or intraarterial administration, is preferable. Preferably, the composition of the present invention can be locally administered to a site to be treated (an affected site, such as a lesion site of central nervous system). Local administration of the composition of the present invention to the central nervous system lesion site of a patient is advantageous because the immune system of the patient is not very active inside the blood-brain barrier. That is to say, the opportunities of the immunological rejection of the host to a nerve cell to be transplanted can be reduced, and even in a case in which an immunosuppressive agent is still required, the opportunities of graft survival are increased. Such local administration is also advantageous in that a transplanted cell can be more precisely targeted to the central nervous system lesion.

When the composition of the present invention is transplanted into a central nervous system lesion, the transplantation can be carried out by stereotaxic surgery. In this case, the patient is anesthetized. The head of the patient is place in an MRI compatible stereotaxic frame, and a micropositioner equipped with a microinjector is disposed on the braincase. In order to expose a dural region located directly above a target site, a burr hole is formed on the cranium of the patient, using a dental drill or another appropriate appliance.

An analgesic (for example, buprenorphine) and an antibiotic (for example, cefazolin; 50 mg/kg; IM; 2 times per day×5 days) may be administered, as necessary, as a part of the procedures of surgical operation/postoperative treatments. After completion of the surgical operation, administration of an antibiotic may be continuously carried out for a long period of time, and preferably for 30 days after the surgical operation, so that it may suppress opportunistic infection.

Moreover, an immunosuppressive agent may be administered together with the composition of the present invention, as necessary. Particularly when the composition of the present invention is systemically administered, such immunosuppressive agent can suppress the rejection of transplanted cells by the immune system of the patient. Specific examples of such immunosuppressive agent include, but are not limited to: antimetabolites such as azathioprine; alkylating agents such as cyclophosphamide; and folic acid antagonists such as methotrexate or mercaptopurine (6-MP), mycophenolate (CellCept), cyclosporine-A, and tacrolimus (FK-506). Such immunosuppressive agent may be administered via various administration routes, such as oral, intraperitoneal, and intravenous administrations. The applied dose of such immunosuppressive agent is changed depending on the properties of the immunosuppressive agent and the patient. For example, administration of the immunosuppressive agent may be started on the day of transplantation (approximately 4 hours after the treatment), and thereafter, the immunosuppressive agent may be continuously administered at intervals of 24 hours. The dose is preferably approximately 0.5 mg/kg/day to approximately 100 mg/kg/day, and more preferably approximately 5 mg/kg/day to approximately 50 mg/kg/day. In the case of intravenous injection, it can be administered as a bolus at a flow rate of preferably approximately 0.005 to approximately 0.100 RL/min, and more preferably approximately 0.050 μL/min.

EXAMPLES

The Present Invention will be Described more in Detail in the Following Examples.

In the following examples 1-8, "SB623" manufactured by Sanbio (www.san-bio.com/product/pipeline.php) was used as a model of bone marrow stromal cell-derived neural precursor cells which were obtained by (1) introducing a nucleic acid comprising Notch sequences, wherein said Notch sequences consist of sequences encoding a Notch intracellular domain, and (2) culturing said bone marrow stromal cells such that said bone marrow stromal cells differentiate into neural precursor cells, wherein the resultant differentiated cells are offspring of bone marrow stromal cells into which said nucleic acid has been introduced.

In the following examples 9, "SB618" manufactured by SanBio (www.san-bio.com/product/pipeline.php) was used as a model of bone marrow stromal cell-derived Schwann cells which were obtained by (1) culturing bone marrow stromal cells (BMSC) in a standard essential culture medium supplemented with a serum, (2) adding a reducing agent to said culture medium, and further culturing said cells, (3) adding retinoic acid to said culture medium, and further culturing said cells, and (4) adding forskolin, and/or a differentiation, survival and growth stimulating factor which acts on nerves and glial cells to said culture medium, and further culturing said cells. Moreover, CBE3 as described below was prepared as a recombinant gelatin (described in WO2008-1 03 041).

CBE3
Molecular weight: 51.6 kD
Structure: Gly-Ala-Pro[(Gly-X—Y)63]3Gly
Number of amino acids: 571
RGD sequence: 12
Imino acid content: 33%

Almost 100% of amino acids adopt a repeated structure of Gly-X—Y.

The amino acid sequence of CBE3 does not contain serine, threonine, asparagine, tyrosine, and cysteine.

CBE3 has an ERGD sequence.

Isoelectric point: 9.34

Amino acid sequence (SEQ ID NO: 1 in the sequence listing) (the same as SEQ ID NO: 3 described in WO2008/103041, but the X at the end was corrected to "P".)

GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)3G

In addition, as a model of animal gelatin, "APAT" manufactured by Nippi, incorporated was used.

Example 1

Preparation of Biocompatible Polymer Particles

A 18 ml of 3% Glutaraldehyde solution was added into 162 ml of 10% (w/v) CBE3 aqueous solution. The mixture was left at 4° C. for 18 h to make a hydro gel. The hydro gel was freeze dried and milled to make small pieces of CBE3 particles. The photographs of the obtained CBE3 particles are shown in FIG. 1.

Example 2

In Vitro Cell Viability on Rat Hippocampal Slice

10% (v/v) of CBE3 particles or animal gelatin particles were suspended in a medium (α-MEM; 10% FBS; 1% PS). Thereafter, GFP-labeled Notch intracellular gene induced bone marrow derived cells (SB623 manufactured by Sanbio) were suspended in each solution. The thus produced cell suspension was added onto the hippocampal section of a P9 rat placed on a 12-well plastic plate.

The section was then incubated in a $CO_2$ incubator at 37° C. One, two, five, nine and fourteen days after initiation of the incubation, cells expressing GFP on the section were observed under a fluorescent microscope, and the number of such cells was counted. The cells that expressed GFP were considered to be surviving cells. Thus, the survival rate of the cells was evaluated as a ratio with respect to the number of cells 1 day after initiation of the inoculation. The results are shown in FIG. 2.

The survival rate of the cells was improved by the effects of CBE3 particles or animal gelatin particles.

Example 3

In Vitro Cell Viability in Ultra Low Attachment Culture Plate 0.01 cm3/well of CBE3 and animal gelatin particles in 500 ul of α-MEM are placed in a Ultra Low Attachment Culture Dish (manufactured by Corning). Thereafter, 50,000 of Notch intracellular gene induced bone marrow derived cells (SB623 manufactured by Sanbio) were plated and incubated in a $CO_2$ incubator at 37° C., 2 hours and one, four, and seven days after initiation of the incubation, samples are filtered by a cell strainer (mesh size 40 um) and DNA is extracted from recovered samples by dissolving in papain solution (2.5 mU/ml papain, 5 mM L-cystein, 5 mM EDTA) at 60° C. overnight. By using standard curve, number of cells on particles was counted. Because live cells adhere on particles and dead cells do not, the survival rate of the cells was evaluated as a ratio with respect to the number of cells 0 day (2 hours) after plating.

As shown in FIG. 3, the survival rate of the cells was improved by CBE3 particles or animal gelatin particles.

Example 4

Cell Adhesion on CBE3 Particles 5.8% of CBE3 particles and 20,000 cells/ul of cells were suspended in alpha-MEM. They were incubated in a $CO_2$ incubator at 37° C. for 4 h with gentle rocking. Thus, the sample was transferred to 6 well cell culture plate and stained in Calsein-AM solution (5 ul Calsein-AM from Invitrogen in 10 ml PBS) for 30 min at 37° C. Then pictures of the samples were taken by fluorescent microscopy.

As shown in FIG. 4, cells were obviously attached on a CBE3 particle.

Example 5

Number of Cells on CBE3 Particles 5.8% of CBE3 particles and 20,000 cells/ul of cells were suspended in alpha-MEM. They were incubated in a $CO_2$ incubator at 37° C. for 4 h with gentle rocking. Then, the mixture was transferred to a cell-strainer (mesh size 40 um, product of Fisher Bioscience). The sample remained on the cell-strainer was recovered into 15 ml conical tube and dissolved in 4 ml of papain solution (2.5 mU/ml papain, 5 mM L-cystein, 5 mM EDTA) at 60° C. overnight to extract DNA from cells. By using standard curve, number of cells on particles was counted.

As shown in FIG. 5, 57% (11,400 cells/ul) of cells were attached on the particles.

Example 6

Transplanted Cell Viability in Stroke Model Rat Brain (1Month Post-TP)

As a stroke model, transient middle cerebral artery occlusion (MCAo) model rats were used. 1 month after stroke, composition of cells and CBE3 particles or cell suspension was transplanted into their striatum.

To obtain the composition of cells and CBE3 particles, 5.8% of CBE3 particles and 20,000 cells/ul of cells were suspended in alpha-MEM. They were incubated in a $CO_2$ incubator at 37° C. for 4 h with gentle rocking. Then, the composition was transplanted into brains of stroke model rats.

1 month after transplantation, rats were sacrificed and their brains were removed. Then, the brains were cut into 25 um sections.

The sections were stained with anti-HuNu (product of Chemicon) as a primary antibody, and Alexa 488-conjugated anti-mouse antibody as a secondary antibody. Then the number of HuNu positive cells was counted for all animals.

As shown in FIG. 6, CBE3 particles improve the viability of cells transplanted into brains of stroke model rats (Cell Only: n=6, Cell+Particle: n=6).

As described in US. Patent Application No. 2006/0216276, the efficacy of the treatment by Notch introduced cell transplantation is dose dependent (FIGS. 1 to 28 in US. Patent Application No. 2006/0216276). On the other hand, cell viability is essentially the same for any dose of cells (FIG. 30 in US. Patent Application No. 2006/0216276). As a result, the number of cells alive in the brain is highly dose dependent (FIG. 29 in US. Patent Application No. 2006/0216276). These facts lead to an idea that the efficacy of treatment is dose dependent because the number of cells alive in a brain is dose dependent. Therefore, it is considered that the efficacy of treatment improves if more cells are alive in a brain.

One way to improve the number of cells alive in a brain is to transplant more cells in the brain. However, the concentration of cells and the volume allowed to inject into a brain is limited. Accordingly, the best way to improve the number of cells alive in a brain is to improve the cell viability after transplantation into a brain because it is consistently low.

Thus, it is considered that to improve the cell viability after transplantation into a brain is the best way to improve the efficacy for treatment.

Example 7

Preservation of Host Neuron in Stroke Model Rat Brain (1Month Post-TP)

Some of the sections obtained as described in Example 6 were stained by cresyl violet. By those sections, preservation of host neuron in ischemic striatum was estimated. Cresyl violet-stained neurons were counted in four 0.14 $mm^2$ regions of the ischemic striatum and corresponding four areas of the intact side (FIG. 7). Host neuron viability was expressed as percentage of total number of neurons in ischemic striatum against total number of neurons in the corresponding regions in intact side.

As shown in FIG. 8, the host neuron viability is higher for animals treated by cells with CBE3 particles than those treated by cells only. This means CBE3 particles improve the host neuron preservation. (Cells Only: n=6, Cells+Particles: n=7)

Example 8

Preservation of Myelin in Stroke Model Rat Brain (1Month Post-TP)

Some of the sections obtained as described in Example 6 were stained with anti-MBP (product of Abeam) as a primary antibody, and Alexa 488-conjugated anti-rat antibody as a secondary antibody. Then the area of MBP positive cells was measured.

As shown in FIG. 9, CBE3 particles improve preservation of the myelin of nervous tissue in ischemic striatum of host stroke rats (Cell Only: n=7, Cell+Particle: n=6).

Example 7 and 8 supports the idea that improved viability of transplanted cells leads to high efficacy of the treatment, as mentioned in Example 6.

Example 9

Evaluation of In Vitro Viability of Bone Marrow Stromal Cell-derived Schwann Cells SB618 cell manufactured by SanBio, Inc. was used as a model of bone marrow stromal cell-derived Schwann cells which were obtained by (1) culturing bone marrow stromal cells (BMSC) in a standard essential culture medium supplemented with a serum, (2) adding a reducing agent to said culture medium, and further culturing said cells, (3) adding retinoic acid to said culture medium, and further culturing said cells, and (4) adding forskolin, and/or a differentiation, survival and growth stimulating factor which acts on nerves and glial cells to said culture medium, and further culturing said cells, as described in U.S. Pat. No. 6,989,271.

SB618 cells were cultured in a medium (αMEM, 10% FBS, 1% PS) on glass coated with PDL(poly-d-lysin) or CBE3. After 24 hours, SB618 cells were collected by trypsin treatment, and the cell death rate of SB618 cells was evaluated by trypan blue staining.

As shown in FIG. 10, the death rate (2.0%) on the glass coated with CBE3 was lower than the death rate (3.4%) on the glass coated with PDL which is a standard culture plate for SB618 cells.

The results of Example 9 supports that the cell viability can be improved by using a composition which comprises (a) bone marrow stromal cell-derived Schwann cells which were obtained by (1) culturing bone marrow stromal cells (BMSC) in a standard essential culture medium supplemented with a serum, (2) adding a reducing agent to said culture medium, and further culturing said cells, (3) adding retinoic acid to said culture medium, and further culturing said cells, and (4) adding forskolin, and/or a differentiation, survival and growth stimulating factor which acts on nerves and glial cells to said culture medium, and further culturing said cells, as described in U.S. Pat. No. 6,989,271 (namely, said Schwann cells are obtained by differentiating bone marrow stromal cell by certain procedure) and (b) a biocompatible polymer, as compared with a case where only the cells are cultured.

The bone marrow stromal cell-derived Schwann cells which are obtained by (1) culturing bone marrow stromal cells (BMSC) in a standard essential culture medium supplemented with a serum, (2) adding a reducing agent to said culture medium, and further culturing said cells, (3) adding retinoic acid to said culture medium, and further culturing said cells, and (4) adding forskolin, and/or a differentiation, survival and growth stimulating factor which acts on nerves and glial cells to said culture medium, and further culturing said cells, as described in U.S. Pat. No. 6,989,271, and the bone marrow stromal cell-derived skeletal muscle cells which are obtained by (1) adding (i) a cyclic AMP (cAMP) increasing agent or a cAMP analogue, and (ii) a cell differentiation stimulating factor comprising bFGF, PDGF-AA, and neuregulin to a culture of bone marrow stromal cells wherein said bone marrow stromal cells are not treated with a demethylating agent, and culturing the cells; (2) introducing a Notch gene into the cells obtained in (1), and culturing the cells and (3) adding a Notch ligand to the culture obtained in (2), and culturing the cells, as described in U.S. Pat. No. 7,718,429, can be regarded as a same type cell as SB623 cell which was obtained by differentiating bone marrow stromal cells by certain procedure. Therefore, Example 9 supports that the cell viability after transplantation can be improved by using a composition which comprises the cells described in U.S. Pat. No. 6,989,271 or U.S. Pat. No. 7,718,429 and a biocompatible polymer, as compared with a case where only the cells were transplanted.

What is claimed is:

1. A method for treating injured central nervous system, which comprises
   freeze-drying a hydrogel of (B) a biocompatible polymer followed by milling to prepare particles; and
   administering to a patient suffering from injured central nervous system a therapeutically effective amount of a composition comprising (A) any cells of the following (a) and (b), and (B) the particles of the biocompatible polymer:
   (a) bone marrow stromal cell-derived neural precursor cells which are obtained by (1) introducing a nucleic acid comprising Notch sequences, wherein said Notch sequences consist of sequences encoding a Notch intracellular domain, and (2) culturing said bone marrow stromal cells such that said bone marrow stromal cells differentiate into neural precursor cells, wherein the resultant differentiated cells are offspring of bone marrow stromal cells into which said nucleic acid has been introduced; and
   (b) bone marrow stromal cell-derived Schwann cells which are obtained by (1) collecting bone marrow stromal cells from bone marrow, and culturing said cells in a standard essential culture medium supplemented with a serum; (2) adding a reducing agent to said culture medium, and further culturing said cells; (3) adding retinoic acid to said culture medium, and further culturing said cells; and (4) adding forskolin, and/or a differentiation, survival and growth stimulating factor which acts on nerves and glial cells to said culture medium, and further culturing said cells to obtain said bone marrow stromal cell-derived Schwann cells;

wherein the injured central nervous system is a cerebral infraction caused by the necrosis of brain tissues due to ischemia, Parkinson's disease, or spinal cord injury caused by damaging the spinal cord by strong external force.

2. The method according to claim 1, wherein the biocompatible polymer is a gelatin.

3. The method according to claim 1, wherein the biocompatible polymer is a recombinant gelatin having an amino acid sequence derived from a partial amino acid sequence of collagen.

4. The method according to claim 3, wherein the recombinant gelatin has a 4 repetition of a sequence characteristic for collagen represented by Gly-X—Y wherein each of X and Y independently represents any given amino acid, wherein a plurality of Gly-X—Y may be identical to or different from one another, and the recombinant gelatin has a molecular weight of 2 KDa to 100 KDa.

5. The method according to claim 3, wherein the recombinant gelatin has a repetition of a sequence characteristic for collagen represented by Gly-X—Y wherein each of X and Y independently represents any given amino acid, wherein a plurality of Gly-X—Y may be identical to or different from one another, and the recombinant gelatin has a molecular weight of 10 KDa to 90 KDa.

6. The method according to claim 3, wherein the recombinant gelatin has a repetition of a sequence characteristic for collagen represented by Gly-X—Y wherein each of X and Y independently represents any given amino acid, wherein a plurality of Gly-X—Y may be identical to or different from one another, and the recombinant gelatin comprises two or more sequences of cell adhesion signals in a single molecule.

7. The method according to claim 6, wherein the cell adhesion signal has an amino acid sequence represented by Arg-Gly-Asp.

8. The method according to claim 3, wherein the recombinant gelatin is represented by the following formula:

A-[(Gly-X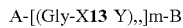 Y)$_n$]$_m$-B wherein A represents any given amino acid or amino acid sequence; B represents any given amino acid or amino acid sequence; each of an n number of X independently represents any given amino acid; each of an n number of Y independently represents any given amino acid; n represents an integer of 3 to 100; m represents an integer of 2 to 10; and further, an n number of Gly-X—Y may be identical to or different from one another.

9. The method according to claim 3, wherein the recombinant gelatin is represented by the following formula:

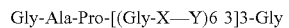

wherein each of 63 X units independently represents any given amino acid; each of 63 Y units independently represents any given amino acid; and 63 Gly-X—Y units may be identical to or different from one another.

10. The method according to claim 3, wherein the recombinant gelatin has: (1) the amino acid sequence shown in SEQ ID NO: 1, or (2) an amino acid sequence showing a homology of 80% or more with the amino acid sequence shown in SEQ ID NO: 1 and having the property of adhering to a nerve cell or a cell capable of differentiating a nerve cell.

11. The method according to claim 3, wherein the recombinant gelatin crosslinked.

12. The method according to claim 3, wherein the crosslinking is carried out with an aldehyde, a condensing agent, or an enzyme.

13. The method according to claim 1, wherein the composition is administered locally.

14. The method according to claim 1, wherein the composition is administered to the central nervous system of the patient.

15. The method according to claim 1, wherein the biocompatible polymer (B) is particles of a biocompatible polymer, wherein the cells are attached on the particles.

16. The method according to claim 1, wherein the biocompatible polymer is a non-naturally occurring recombinant gelatin having an amino acid sequence derived from a partial amino acid sequence of collagen.

17. The method according to claim 1, wherein the composition comprises a pharmaceutically acceptable carrier, and the cells and the particles of the biocompatible polymer are suspended in the carrier.

18. The method according to claim 1, wherein the concentration of cells in the composition is approximately 1,000 cells/micro L and 50,000 cells/ micro L.

* * * * *